(12) United States Patent
Gunnarsson

(10) Patent No.: US 6,247,924 B1
(45) Date of Patent: Jun. 19, 2001

(54) SELF-CLEANING ROTATING DENTIST'S MIRROR

(76) Inventor: Stefan Gunnarsson, Spelmansgatan 24, S -371 49 Karlskrona (SE)

( * ) Notice: Subject to any disclaimer, the term of this patent is extended or adjusted under 35 U.S.C. 154(b) by 0 days.

(21) Appl. No.: 09/423,308

(22) PCT Filed: May 7, 1998

(86) PCT No.: PCT/SE98/00832

§ 371 Date: Nov. 12, 1999

§ 102(e) Date: Nov. 12, 1999

(87) PCT Pub. No.: WO98/51233

PCT Pub. Date: Nov. 19, 1998

(30) Foreign Application Priority Data

May 12, 1997 (SE) .................................................. 9701744

(51) Int. Cl.[7] .................................................... A61B 1/24
(52) U.S. Cl. ................................................................ 433/30
(58) Field of Search .......................... 433/30, 31; 359/508

(56) References Cited

U.S. PATENT DOCUMENTS

| | | | | |
|---|---|---|---|---|
| 3,859,987 | * | 1/1975 | Holstad | 433/30 |
| 4,261,637 | * | 4/1981 | King | 433/30 |
| 4,320,937 | * | 3/1982 | Schuwerk | 350/62 |
| 4,408,991 | * | 10/1983 | Engel | 433/30 |

* cited by examiner

*Primary Examiner*—John J. Wilson
(74) *Attorney, Agent, or Firm*—Dennison, Scheiner, Schultz & Wakeman

(57) ABSTRACT

A self-cleaning dentist's mirror is disclosed which includes a hollow handle having a housing at one end and a mirror rotatably supported in the housing on a spindle. Turbine blades are attached to the bottom of the mirror, and the handle is connected to a suction device that draws air into the housing past the edges of the mirror and the turbine blades to rotate the mirror and remove water and other foreign substances from the mirror surface.

10 Claims, 3 Drawing Sheets

SELF-CLEANING ROTATING DENTIST'S MIRROR

The invention relates to instruments as described in the preamble to claim 1.

BACKGROUND ART AND TECHNICAL FIELD

In his/her daily work a dentist must use a mouth mirror to enable him/her to see everywhere inside the oral cavity. A conventional mouth mirror consists of a narrow handle with a circular mirror attached to one end. The mirror surface is usually angled in relation to the axis of the handle in order to facilitate inspection of all surfaces of the teeth.

The water cooling the high-speed drill is a considerable problem since it deteriorates vision in the mirror. The surface of the mirror is also contaminated by condensation, drill chips and saliva. The cooling water must also be removed by a special suction device since the conventional saliva suction device is insufficient. Since one of the dentist's hands is holding the mirror and the other the drill, a nurse usually assists with a suction device which helps to maintain clear vision on the mouth mirror.

It is known to remove foreign substances from the mirror with the aid of centrifugal force on rotating mirrors. European patent 0 387 216 A1 describes such an arrangement. It shows a mirror provided with a turbine and operating by compressed air. Foreign substances and water are not removed from the oral cavity, only from the mirror.

British patent specification GB 1 255 719 shows cleaning of the mirror with water jets, the water then being evacuated by vacuum suction. A dependent claim also talks of a mirror with rotation which, according to the description, is obtained from compressed air that can operate a small turbine.

The compressed-air operation in the known solutions entails complicated constructions and expensive installation costs. Many dentists therefore refrain from this equipment and instead use a conventional dentist's mirror without any self-cleaning.

BRIEF DESCRIPTION OF THE INVENTION

The object of the invention is to solve the problem described in the introduction in a better manner than is possible using known technology. With this object in mind the invention is characterized by the definitions in the characterizing part of claim 1. An instrument of this type requires no installation costs since it is connected directly to the suction nozzles forming a part of every dentist's equipment. The diameter of the vacuum shaft and volume of the chamber in which the mirror is located are made sufficiently large to obtain the strong suction necessary to draw to it the aerosol formed by the cooling water from the high-speed drill.

Combining the suction device with a rotating mirror provides a mirror with free vision and strong suction in the same instrument. The nurse need not assist during drilling and considerable savings can be made.

The greatest advantage, however, is the dentist's satisfaction and precision in being able to see in the mirror without having to constantly interrupt the procedure in order to wipe it.

BRIEF DESCRIPTION OF THE DRAWINGS

Embodiments of the invention are shown schematically in the accompanying drawings.

DESCRIPTION OF EMBODIMENTS

Figure 1:
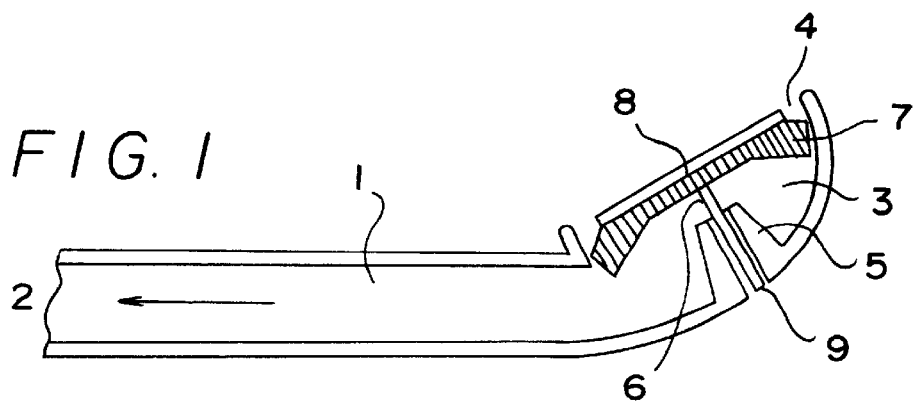
FIG. 1 shows the instrument from the side, in section.
Figure 2:
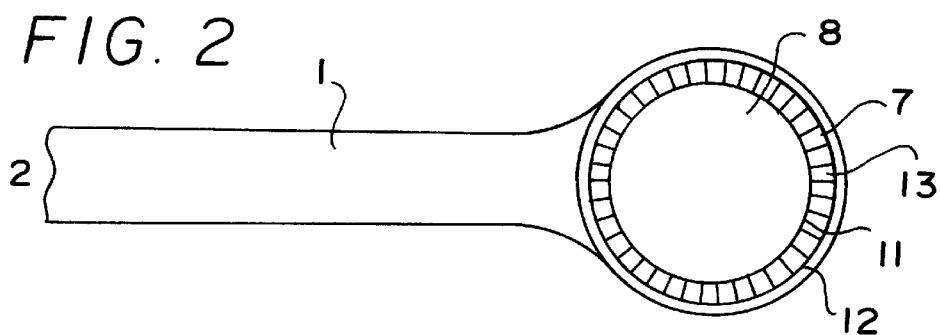
FIG. 2 from the mirror side.
Figure 3:
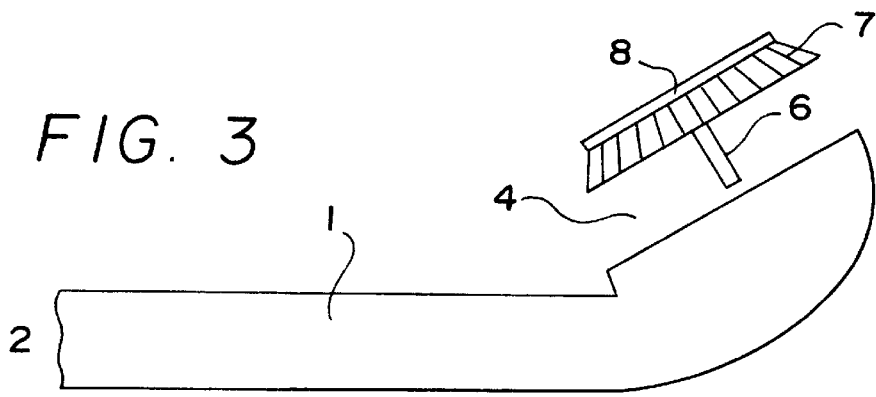
FIG. 3 from the side with the turbine-mirror-spindle unit detached.
Figure 4:
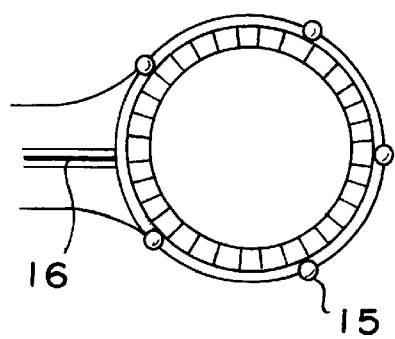
FIG. 4 from the mirror side with illumination

The instrument comprises a longitudinally extending shaft 1, suitably cast in plastic, one end 2 of which is connected to a vacuum suction device. The other end is provided with a chamber 3 with a circular opening 4 inclined backwards and to the side in relation to the normal direction of movement of the air in the shaft. In the opening is a mirror with fixed blade members 7 to cause rotation, to which the mirror is attached. The blade members constitute parts of a turbine 7 having a spindle 6 journalled at a part of a housing (5) demarcating the chamber, said housing being located opposite the opening. The housing may be provided with roller bearings 14.

A gap 13 is provided between the peripheral limit 11 of the mirror and the limit 12 of the opening. The gap is covered at least partially by the blade members, without their coming into contact with the chamber housing. Air is drawn in through the gap and drives the turbine, which causes the mirror to rotate. Due to the rotation the foreign substances on the mirror are thrown out peripherally, sucked into the gap and removed from the mouth. The gap can of course be given a width determined by trial and error. A suitable width has been found to be in the order of 0.1–3.0 mm but may naturally be a different size. In most cases the mirror is circular. However, the circumference 12 of the chamber 3 may be asymmetrical in relation to the circumference of the mirror.

Figure 5:
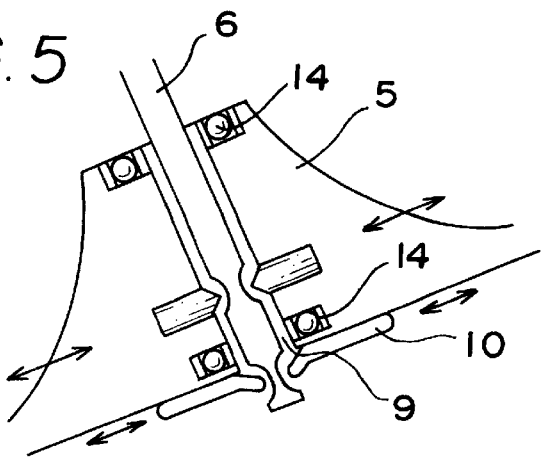
FIG. 5 from the side, locking alternative for the spindle.

The spindle can be d is mantled from the bearing by means of an openable locking device. The locking device may be either inside or outside the bearing. In FIG. 5 the locking device is situated inside the bearing, as indicated in broken lines. If the locking device is arranged inside the bearing housing, an opening 9 is provided through which the locking device of the spindle can be unlocked with an instrument so that turbine, mirror and spindle can be removed for cleaning and sterilization.

Figure 6:
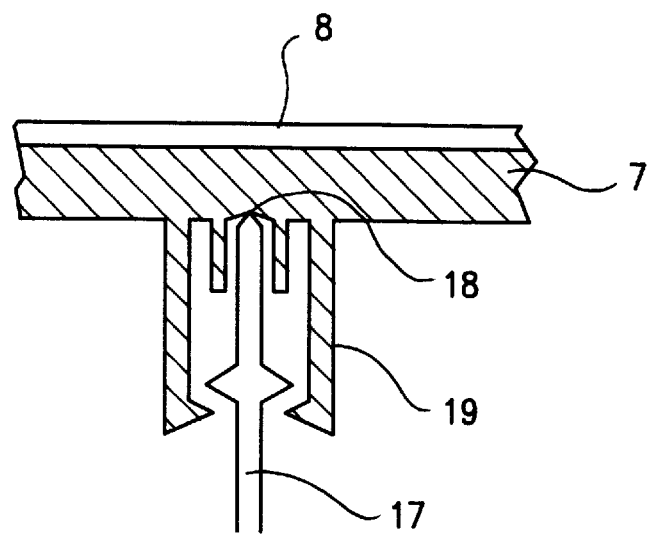
FIG. 6 a section through an alternative bearing.
Figure 7:
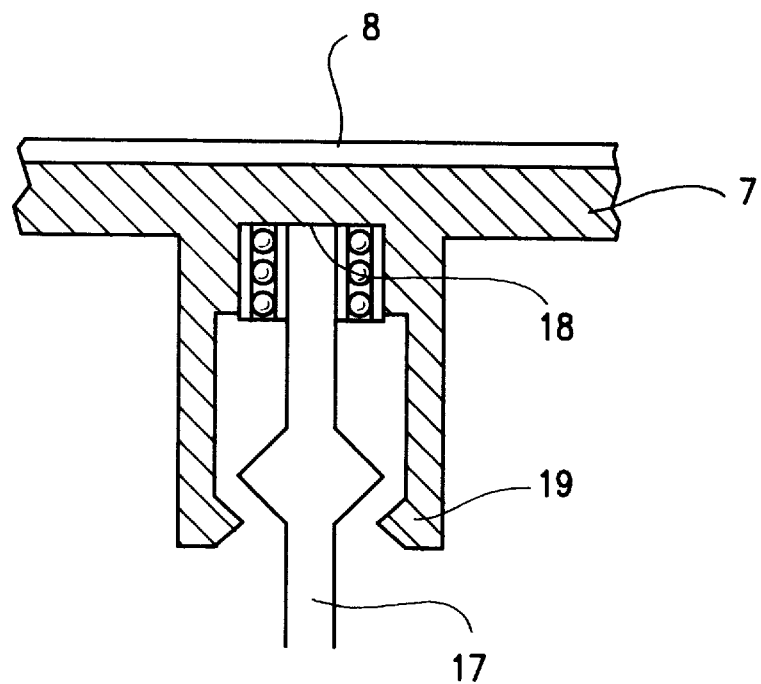
FIG. 7 a section through a second alternative bearing.

In the embodiment shown in FIG. 6 the mirror with blade members and turbine rest against a fixed dismantlable spindle 17 in a hub 18 on the turbine 7. The hub may be provided with roller bearings as shown in FIG. 7. The spindle may even be replaced by an upright or the like extending from the chamber housing. The turbine mirror can be locked axially by a simple snap arrangement. As a result of the vacuum, the mirror and turbine are pressed against the fixed spindle and the rotary gyro action ensures that the locking mechanism (19) attached on the turbine and loosely anchored against the spindle, is for the most part not touched. This gives low friction and high rotational speed.

Figures 8, 9, 10, 11, 12:
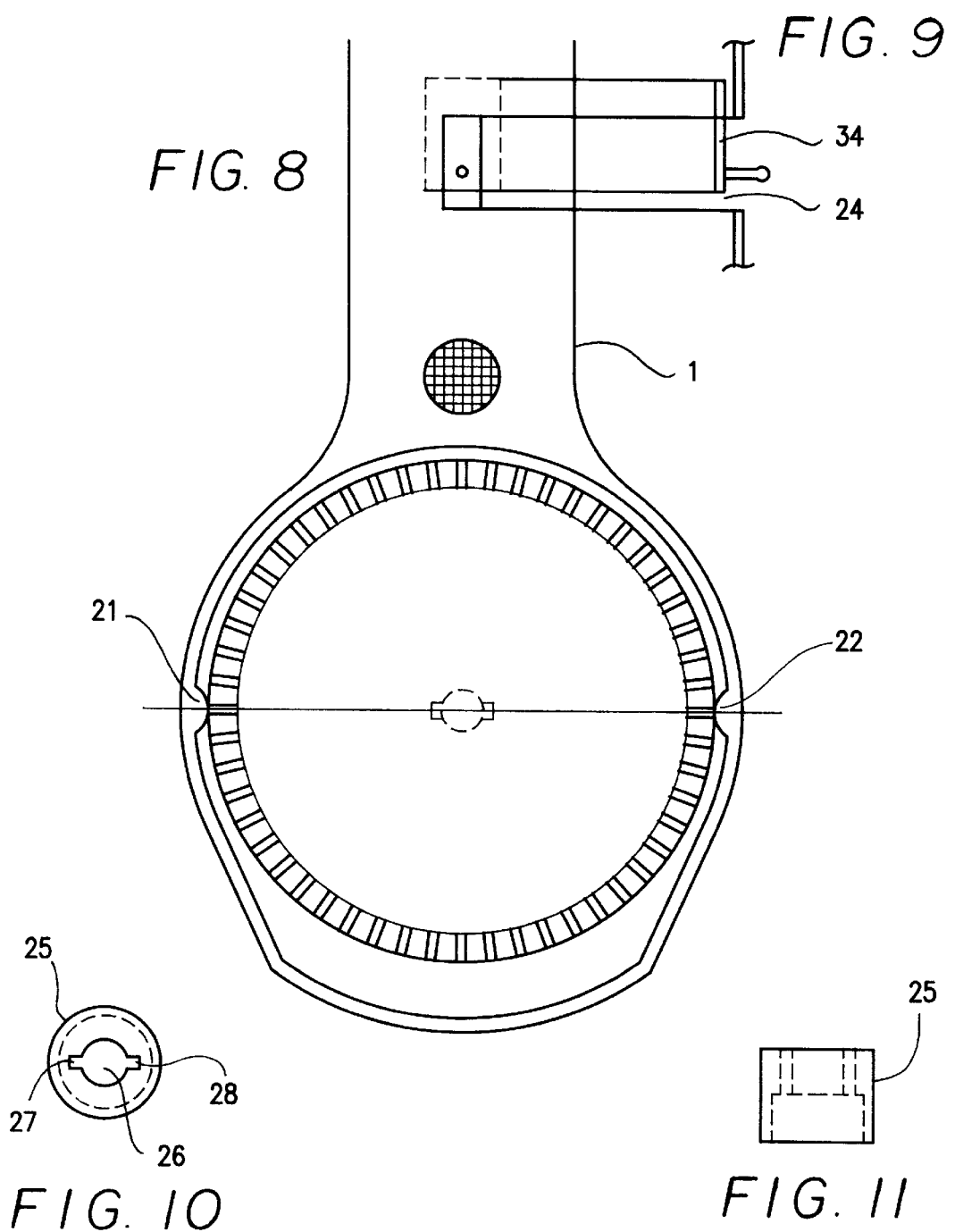
FIG. 8 shows the front part of the instrument with movement pin in axial direction for regulating the flow of medium.
FIG. 9 shows the flow control for the flow of medium in the handle of the instrument.
FIG. 10 shows a bearing pin for the spindle of the mirror, seen from above.
FIG. 11 shows the same pin as in FIG. 10, seen from the side.
FIG. 12 shows the chamber with journalling for the spindle of the mirror, and stop(s) for t he mirror spindle.

FIGS. 8 and 12 show how axial displacement of the mirror 8 upwards is prevented by one or more inwardly directed lugs around the circumference of the chamber 3. In the present case two opposing lugs 21 and 22 are provided, the distance between them being less than the diameter of the mirror or turbine so that the mirror or turbine must be snapped over the lugs in order to assume operating position. A pin 25 is secured in the bottom of the chamber, the upper end of the pin having a hole 26 with substantially the same diameter as the spindle 30 of the mirror 8. This spindle 30 is provided at its lowermost end with two transverse, outwardly directed, opposing wings 31 and 32. Recesses 27 and 28 are provided in the pin 25 for these wings. The pin 25 is provided at its lower end with a cavity having large diameter so that the spindle 30 with wings 31 and 32 can rotate freely. The end of the spindle 30 has a tip 33 in contact with the bottom of the chamber 3.

The shaft 1 can be throttled with suitable known means so that the mirror 8 acquires the desired rotational speed. It is also possible to allow suction force to leak in through the shaft 1, as can be seen from the slide 34 in FIG. 9 where the shaft 1 is provided with an aperture 24, the opening of which may vary from 0 up to fully opened.

The volume of air flowing can be varied by varying the diameter of the mirror surface, and thus the size of the gap. If a large suction effect is desired, the surface area of the mirror must be decreased and vice versa. The field of vision in the mirror can also be increased or decreased as desired by making the surface of the mirror convex or concave. The rotational speed and the flow of air can be regulated by the number, angle and size of the blade members. Several alternative mirror turbine units can thus be used as the need arises.

Light source(s) 15 may be placed at the edge of the opening 4, which are so adjusted that the operation area is illuminated as well as possible. The light can be obtained via fiber optics or in some other way. Cable or fiber 16 for illumination is cast into or attached on the shaft.

What is claimed is:

1. Dental instrument having a mirror (8) arranged rotatably in an opening (4), open to the atmosphere, of a chamber (3) connected to a shaft (1), the mirror only partially covering the opening and having fixed blade members (7) to produce rotation, characterized in that the shaft is connected to a vacuum source (2) which, during use of the instrument, sucks air through the opening (4) past the blade members (7) so that the mirror (8) rotates and is at the same time cleaned.

2. Instrument as claimed in claim 1, characterized in that the blade members (7) constitute a part of a turbine to which the mirror (8) is fixed, which turbine is rotationally journalled in relation to a housing (5) demarcating the chamber (3).

3. Instrument as claimed in claim 1, characterized in that the blade members constitute a part of a turbine (7) to which the mirror is fixed, which turbine has a spindle (6, 17) journalled in a bearing at a part of a housing (5) demarcating the chamber, said housing being located opposite the opening.

4. Instrument as claimed in claim 3, characterized in that the spindle can be dismantled from the bearing by means of an openable locking device.

5. Instrument as claimed in claim 1, characterized in that the blade members constitute a part of a turbine to which the mirror is secured, the central parts of said turbine having rotational journalling in relation to a fixed support part (17) arranged via the chamber housing (5).

6. Instrument as claimed in claim 5, characterized in that the support part comprising a spindle (17) which can be dismantled from the housing.

7. Instrument as claimed in claim 1, characterized in that the instrument is provided with illumination.

8. Instrument as claimed in claim 1, characterized in that the mirror is flat.

9. Instrument as claimed in claim 1 characterized in that the mirror is convex.

10. Instrument as claimed in claim 1 characterized in that the mirror is concave.

* * * * *